(12) United States Patent
Tokorotani

(10) Patent No.: US 7,092,556 B2
(45) Date of Patent: Aug. 15, 2006

(54) DATA READER FOR READING BIOLOGICAL DATA FROM CONSTRAINED HUMAN BODY REGION

(75) Inventor: Mitsuhiro Tokorotani, Tokyo (JP)

(73) Assignee: NEC Infrontia Corporation, Kanagawa (JP)

( * ) Notice: Subject to any disclaimer, the term of this patent is extended or adjusted under 35 U.S.C. 154(b) by 533 days.

(21) Appl. No.: 10/061,237

(22) Filed: Feb. 4, 2002

(65) Prior Publication Data

US 2003/0030541 A1  Feb. 13, 2003

(30) Foreign Application Priority Data

Aug. 9, 2001  (JP)  ............... 2001-242203

(51) Int. Cl.
*G06K 9/00* (2006.01)
(52) U.S. Cl. ......................... 382/126; 356/71
(58) Field of Classification Search ............... 382/115, 382/116, 124–127, 209, 217, 218, 224; 340/5.52, 340/5.53, 5.81–5.83; 600/300, 301; 356/71
See application file for complete search history.

(56) References Cited

U.S. PATENT DOCUMENTS 5,926,261 A * 7/1999 Hoshino ............... 356/71
6,692,436 B1 * 2/2004 Bluth et al. ............. 600/300
6,705,990 B1 * 3/2004 Gallant et al. ........... 600/300

FOREIGN PATENT DOCUMENTS

| JP | 60-123061 U | 8/1985 |
|----|-------------|--------|
| JP | 1-38284 B2 | 8/1989 |
| JP | 9-135822 A | 5/1997 |
| JP | 10-198786 A | 7/1998 |
| JP | H10-198785 A | 7/1998 |
| JP | 11-047118 A | 2/1999 |
| JP | 11-123196 A | 5/1999 |
| JP | 11-232423 A | 8/1999 |
| JP | 3042434 B2 | 3/2000 |
| JP | 2001-120521 A | 5/2001 |

* cited by examiner

*Primary Examiner*—Samir Ahmed
(74) *Attorney, Agent, or Firm*—Sughrue Mion, PLLC

(57) ABSTRACT

A data reader constrains a human body region of an examinee in a readout position upon inflation of balloon members. The data reader can safely and reliably constrains the human body region, which is not uniform in outer profile, with a simple structure, and read biological data from the constrained human body region. The data reader is capable of reading biological data from the constrained human body region even when the examinee is not cooperative.

11 Claims, 5 Drawing Sheets

DATA READER FOR READING BIOLOGICAL DATA FROM CONSTRAINED HUMAN BODY REGION

BACKGROUND OF THE INVENTION

1. Field of the Invention

The present invention relates to a data reader for reading biological data from a human body region, and more particularly to a data reader which is capable of constraining a human body region from which biological data is to be read.

2. Description of the Related Art

Data readers for reading biological data such as fingerprint image data and eyeprint image data from examinees are presently available for use in processes of recognizing the examinees. According to a data reader for scanning and reading a fingerprint image, for example, an examinee's finger is placed in the readout position of an optical scanner, and then the optical scanner is operated to scan the finger to read a fingerprint image there from.

Japanese Utility-model Laid-open No. 123061/1985 discloses a device having a guide disposed around a position where an examinee's finger is to be placed.

If the examinee whose fingerprints are to be imaged is a criminal suspect or a child, then the examinee may occasionally be not cooperative enough to have its fingerprints imaged. Unless the examinee is willing to cooperate, it is difficult to place its fingers in the readout position of the data reader within a given time. A data reader disclosed in Japanese Patent Laid-open No. 198786/1998, for example, has an arch-shaped resilient member for constraining a finger in a readout position. With the disclosed data reader, it is difficult to place a finger of a noncooperative examinee safely and reliably in the readout position within a given time.

SUMMARY OF THE INVENTION

It is therefore an object of the present invention to provide a data reader which is capable of constraining a human body region safely and reliably in a readout position and reading biological data from the constrained human body region.

A data reader according to the present invention comprises data reading means, region constraining means, and mode switching means, and reads biological data from a human body region of an examinee. The mode switching means switches the region constraining means to an initial mode in which the human body region is movable. In the initial mode, the human body region is placed in the readout position of the data reading means. Then, the mode switching means switches the region constraining means to a mode in which the human body region is constrained. The region constraining means constrains the human body region in the readout position. The data reading means reads biological data from the human body region constrained in the readout position. Since the biological data is read from the human body region which the latter is being constrained in the readout position, the biological data can reliably be read even when the examinee is not cooperative.

The mode switching means selectively introduces a fluid under pressure into and discharges a fluid from a balloon member of the region constraining means which is inflatable and deflatable. When the balloon member is inflated, the human body region is constrained in the readout position, and when the balloon member is deflated, the human body region is released from the readout position. Accordingly, the human body region, which is not uniform in outer profile, can safely and reliably be constrained with a simple structure.

The mode switching means comprises fluid introducing means, fluid discharging means, and operation control means. The fluid introducing means introduces the fluid under pressure into the balloon member, and the fluid discharging means discharges the fluid which has been introduced under pressure into the balloon member by the fluid introducing means, under the control of the operation control means. Since the inflation and deflation of the balloon member to constrain and release the human body region are controlled by the operation control means, the constraint and release of the human body region based on the inflation and deflation of the balloon member are accurately controlled.

An internal pressure detecting means detects the pressure of the fluid introduced under pressure into the balloon member, and the operation control means controls operation of the fluid introducing means and the fluid discharging means depending on the pressure of the fluid detected by the internal pressure detecting means. The pressure of the balloon member which constrains the human body region upon inflation and releases the human body region upon deflation is controlled to safely and reliably constrain and release the human body region.

If the fluid comprises a gas, then since the balloon member can be inflated by a compressible fluid, the human body region is prevented from being subjected to excessive pressures.

If the fluid comprises ambient air, then no dedicated tank of a sealed gas is required to inflate the balloon member, the balloon member can be inflated with a simple structure.

The balloon member has surface irregularities for presenting an increased frictional resistance to the human body region. When inflated, the frictional resistance presented by the surface irregularities of the balloon member to constrain the human body region is increased, the balloon member can well constrain the human body region.

The data reader further comprises placement detecting means for detecting when the human body region is placed in the readout position. The mode switching means switches the region constraining means depending on the detection by the placement detecting means. Since the human body region is automatically constrained in the readout position when it is placed in the readout position, the human body region can be constrained well in the readout position without the need for a complex control operation.

The placement detecting means detects when the human body region contacts the data reading means. The human body region can automatically be constrained upon contact of the human body region with the data reading means, and the placement of the human body region in the readout position can be detected with a simple structure.

The human body region comprises a hand finger, and the data reading means scans the finger and reads there from a fingerprint image as the biological data while the cylindrical outer circumferential surface of the finger is constrained in a plurality of directions by the region constraining means.

The various means referred to in the present invention may be arranged so as to perform their functions, and may be in the form of dedicated hardware, a computer run by a program with suitable functions, functions realized in a computer by a suitable program, or a combination of these elements. The various means of the present invention may not necessarily be independent means, and some means may be part of other means.

The human body region referred to in the present invention means a certain region of the human body, e.g., a finger or a head. The biological data means certain data that can be read from the human body region, e.g., fingerprint image data, eyeprint image data, or the like.

The above and other objects, features, and advantages of the present invention will become apparent from the following description with reference to the accompanying drawings which illustrate examples of the present invention.

DETAILED DESCRIPTION OF THE PREFERRED EMBODIMENTS

Figure 1:
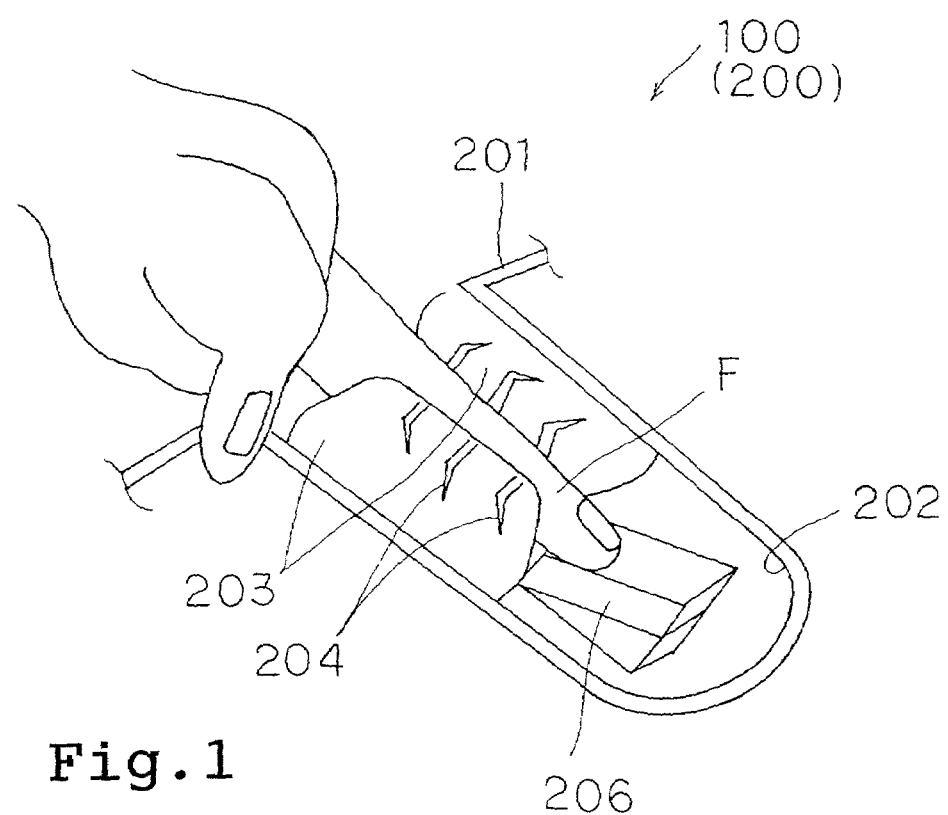
FIG. 1 is a perspective view of a central portion of a data reader according to an embodiment of the present invention.
Figure 2:
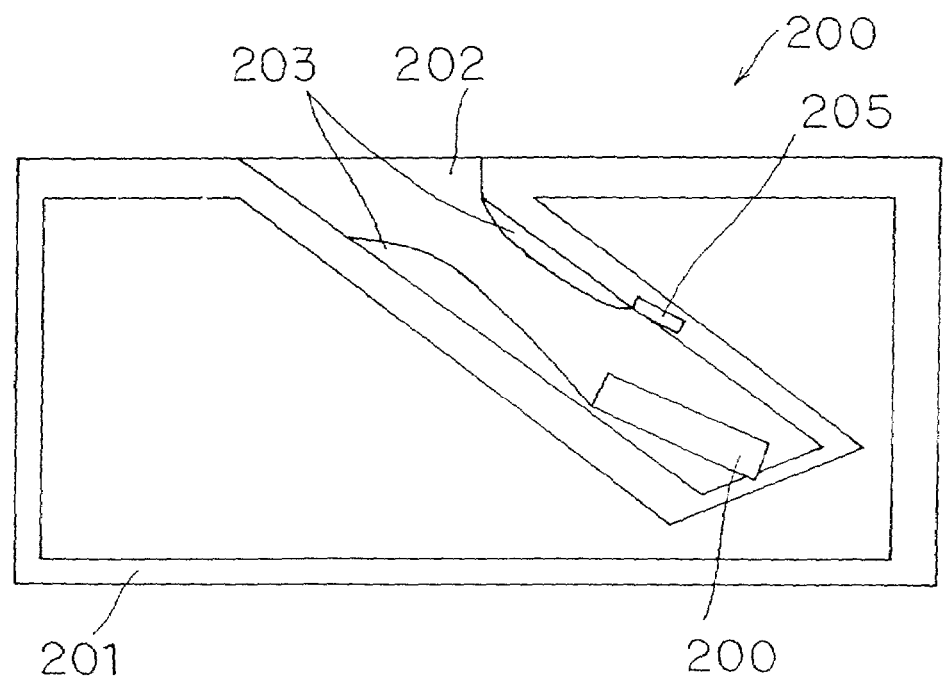
FIG. 2 is a vertical cross-sectional view showing an internal structure of the data reader.
Figure 3:
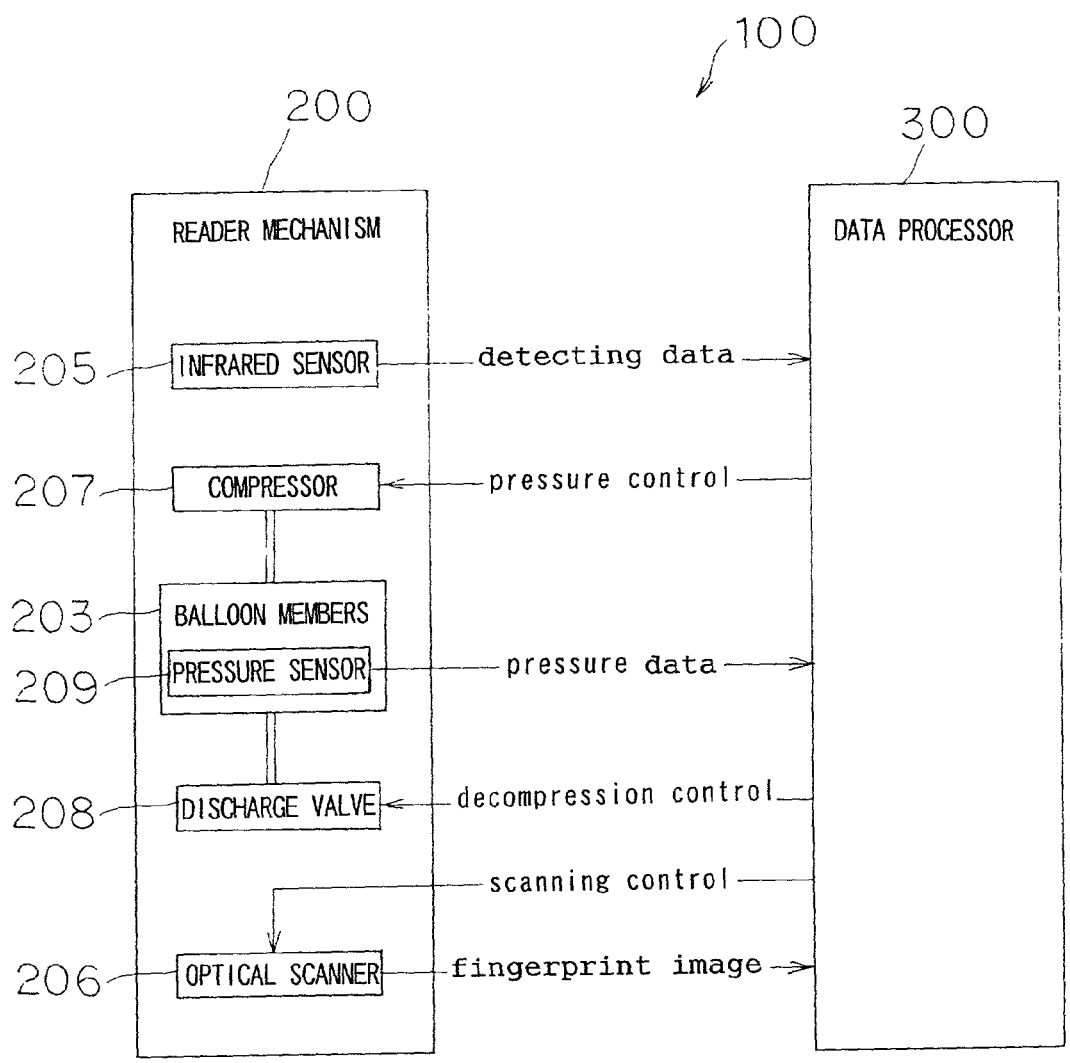
FIG. 3 is a block diagram of an entire arrangement of the data reader.

Data reader 100 according to an embodiment of the present invention has reader mechanism 200 shown in FIGS. 1 and 2 and data processor 300 shown in FIG. 3, such as a personal computer, serving as an operation control means, which is connected to reader mechanism 200.

Figure 4:
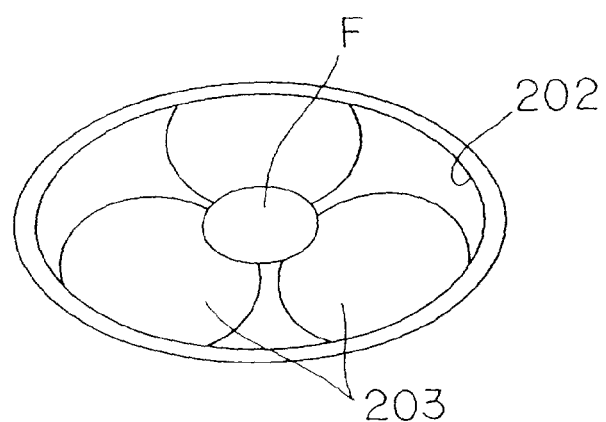
FIG. 4 is a plan view of three balloon members serving as a region constraining means of the data reader.

Reader mechanism 200 has mechanism housing 201 in the form of a rectangular parallelepiped which has cylindrical cavity 202 defined obliquely downwardly in an upper surface thereof for the insertion of finger F of an examinee. As shown in FIG. 4, three balloon members 203 as a region constraining means are mounted on inner surfaces of an upper portion of cavity 202 and oriented in respective three angularly spaced directions.

Balloon members 203 are made of soft rubber having a large coefficient of friction to present a large frictional resistance to finger F, and can be inflated or deflated when a fluid such as ambient air is introduced under pressure into balloon members 203 or discharged from balloon members 203. Balloon members 203 have surface irregularities 204 of an inverted-thorn-shaped cross section for engaging and retaining finger F inserted in cavity 202 against removal there from.

Infrared sensor 205 as a placement detecting means is disposed on an upper surface of a lower portion of cavity 202. Optical scanner 206 as a data reading means is disposed on a lower surface of the lower portion of cavity 202. Infrared sensor 205 serves to detect finger F which has been inserted into cavity 202. Optical scanner 206 serves to scan and read a finger image as biological data from finger F that has been held in contact with the surface of optical scanner 206, which provides a readout position.

To balloon members 203, there are connected a compressor 207 as a fluid introducing means and a discharge valve 208 as a fluid discharging means. A pressure sensor 209 as an internal pressure detecting means is inserted in one of balloon members 203. Compressor 207 introduces under pressure a fluid such as ambient air into balloon members 203. Discharge valve 208 discharges introduced ambient air from balloon members 203. Pressure sensor 209 detects the pressure of ambient air which has been introduced under pressure into balloon members 203.

As shown in FIG. 3, infrared sensor 205, optical scanner 206, compressor 207, discharge valve 208, and pressure sensor 209 are electrically connected to data processor 300. Data processor 300 operates according to a computer program installed therein to control operation of compressor 207, discharge valve 208, and optical scanner 206 based on detected data from infrared sensor 205 and pressure sensor 209, and acquires fingerprint image data from optical scanner 206.

Figure 5:
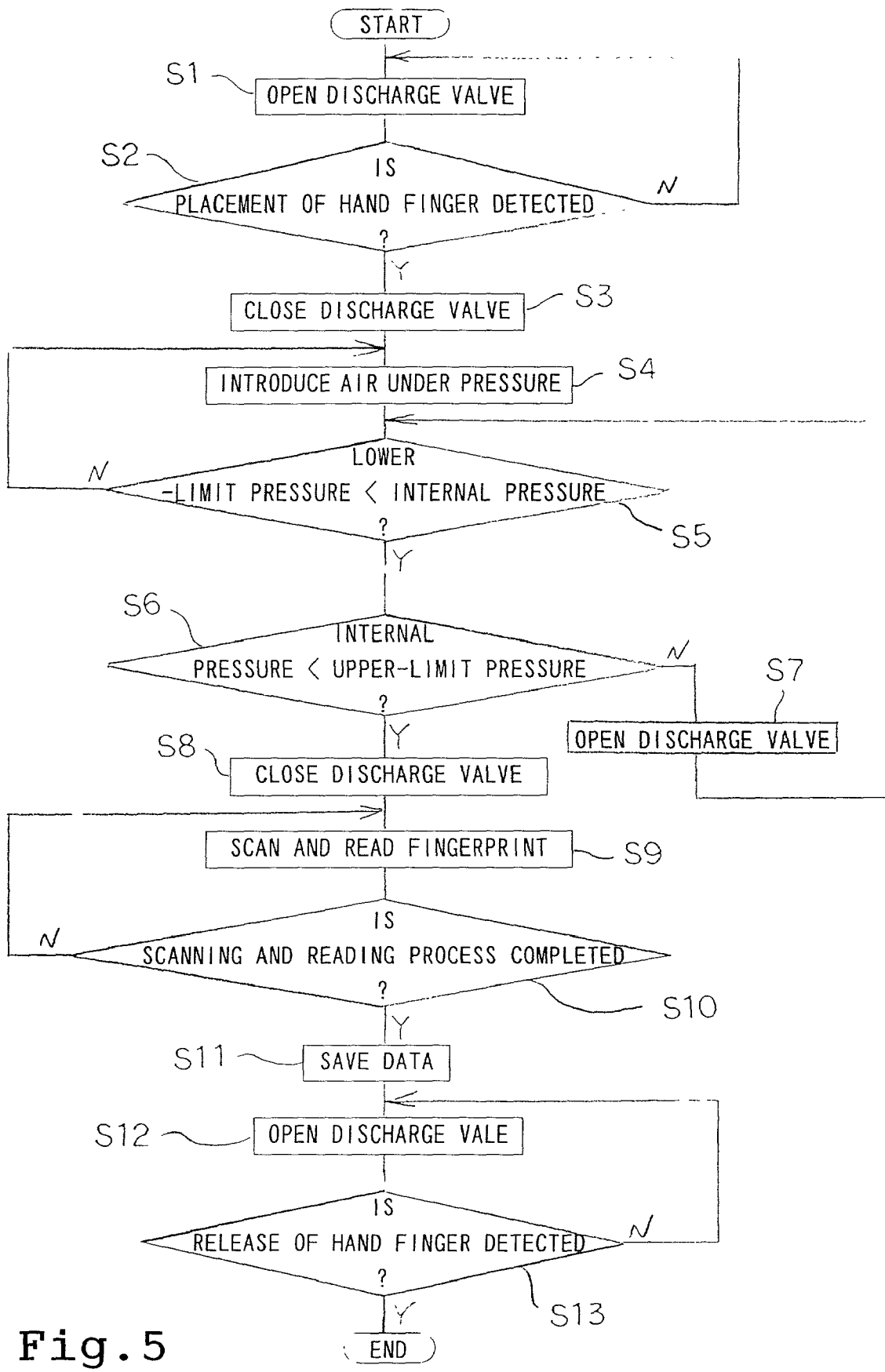
FIG. 5 is a flowchart of a data processing sequence of a data processor of the data reader.

Data reader 100 thus constructed is capable of scanning finger F of an examinee and reading a fingerprint image from finger F. Operation of data reader 100 will be described below with reference to FIG. 5. Data processor 300 opens discharge valve 208 of reader mechanism 200 in step S1. Therefore, three balloon members 203 are deflated, allowing the examinee to insert finger F freely into cavity 202 in mechanism housing 201.

When the examinee inserts finger F to a given position in cavity 202, inserted finger F is detected by infrared sensor 205, which indicates the insertion of finger F to data processor 300 in step S2. Then, data processor 300 closes discharge valve 208 in step S3, and operates compressor 207 in step S4 to introduce ambient air into balloon members 203.

The internal pressure of balloon members 203 is detected at all times by pressure sensor 209 and indicated to data processor 300. Data processor 300 controls compressor 207 to introduce ambient air under pressure to increase the internal pressure of balloon members 203 until the internal pressure of balloon members 203 becomes higher than a given lower-limit pressure in step S5.

If the internal pressure of balloon members 203 becomes higher than a given upper-limit pressure in step S6, then data processor 300 opens discharge valve 208 in step S7. In this manner, the internal pressure of balloon members 203 is regulated within a desired pressure range higher than the lower-limit pressure and lower than the upper-limit pressure. Data processor 300 closes discharge valve 208 in step S8. Balloon members 203 supplied with ambient air under the desired pressure are inflated to constrain inserted finger F under an appropriate pressure, thus securely holding finger F in the readout position.

Having completed the pressure control for balloon members 203 (steps S4 through S8), data processor 300 controls operation of optical scanner 206 to scan finger F and read a fingerprint image there from in step S9. If the canning and reading process is completed in step S10, then data processor 300 saves the data of the fingerprint image together with identification data of the examinee in step S11.

After having saved the data, data processor 300 opens discharge valve 208 in step S12. Balloon members 203 are now deflated to release finger F. If the removal of finger F from cavity 202 is detected by infrared sensor 205 in step S13, then data processor 300 ends its processing sequence.

Since data reader 100 according to the above embodiment reads biological data from the examinee while finger F is being constrained in the readout position, it can well read biological data even when the examinee is not cooperative. Because finger F is constrained in the readout position by the inflation of balloon members 203, finger F whose outer profile may vary from examinee to examinee can safely and reliably be constrained with a simple structure, and can readily be released upon deflation of balloon members 203.

The pressure of the fluid, i.e., ambient air, introduced into balloon members 203 is detected by pressure sensor 209, and data processor 300 controls operation of discharge valve 208 and compressor 207 based on the detected pressure. Consequently, the constraint and release of finger F upon inflation and deflation of balloon members 203 can accurately be controlled, so that finger F can safely and reliably be constrained and released.

Inasmuch as three balloon members 203 constrain the outer circumferential surface of finger F in three directions, they can safely and reliably constrain finger F. As finger F thus constrained is positioned centrally in cavity 202, the fingerprint image can be read from an appropriate position on finger F.

Since balloon members 203 have surface irregularities 204 of a large coefficient of friction on their surfaces, they present a large frictional resistance to finger F when inflated, thus firmly constraining finger F in the readout position.

When finger F is detected by infrared sensor 205, data processor 300 inflates balloon members 203, and when the scanning process performed by optical scanner 206 is finished, data processor 300 deflates balloon members 203. Accordingly, finger F can automatically be constrained and released without the need for a complex process of constraining and releasing finger F.

Balloon members 203 are inflated by ambient air which is a compressible fluid. Therefore, finger F is prevented from suffering excessive pressures. As no dedicated tank of a sealed gas is required to inflate balloon members 203, balloon members 203 can be inflated with a simple structure.

In the above embodiment, finger F is constrained and released by the inflation and deflation of balloon members 203. However, finger F may be constrained and released by an expansible and contractible belt or a displaceable soft pad (not shown).

In the above embodiment, the internal pressure of balloon members 203 is detected by pressure sensor 209 and controlled by data processor 300. However, a fluid may be introduced under a given pressure into balloon members 203 from a pressure source such as a constant-pressure gas container without the need for the detection of the internal pressure of balloon members 203.

Figure 6:
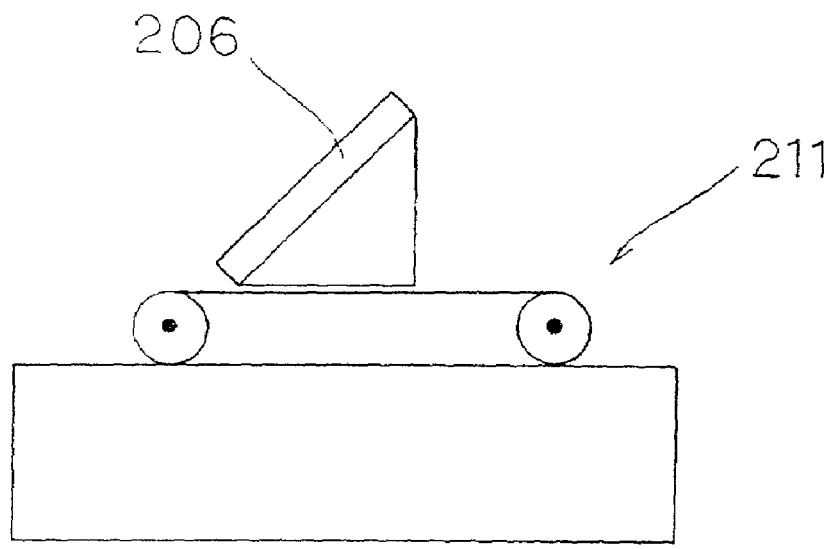
FIG. 6 is a side elevational view of an optical scanner as a data reading means according to a first modification of the present invention.

In the above embodiment, finger F disposed in the readout position of optical scanner 206 is constrained by balloon members 203. However, as shown in FIG. 6, optical scanner 206 may be displaceably supported on belt conveyor 211 and pressed against finger F constrained in a given position by belt conveyor 211. With this modification, since the readout position of optical scanner 206 can be finely adjusted, the accuracy with which to read a fingerprint image can be increased. For example, a fingerprint image of finger F which is very short, such as a child's finger, can be read reliably.

Figure 7:
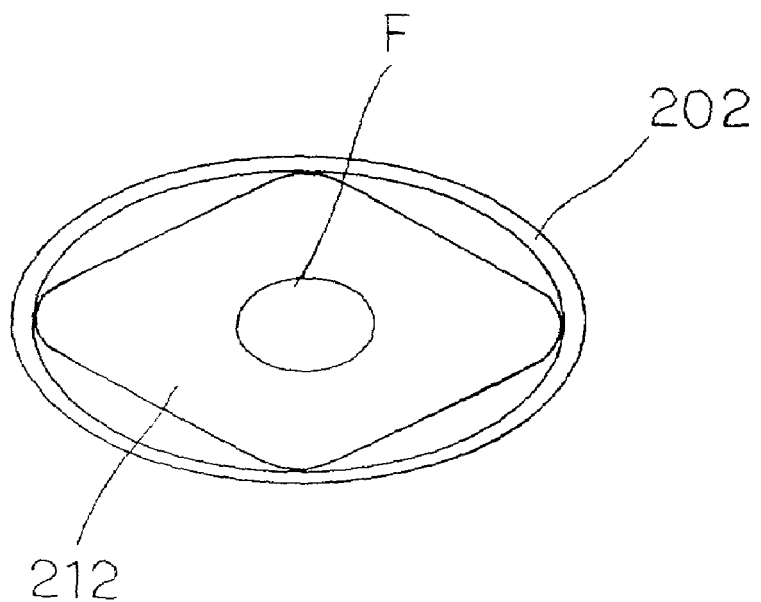
FIG. 7 is a plan view of a balloon member according to a second modification of the present invention.

In the above embodiment, three balloon members 203 constrain the outer circumferential surface of finger F in three directions. However, as shown in FIG. 7, finger F may be constrained in its fully circumferential direction by single annular balloon member 212. In the above embodiment, balloon members 212 are simply and safely inflated by ambient air. However, balloon members 212 may be inflated by a dedicated gas or a liquid such as water or oil.

In the above embodiment, when finger F is detected by infrared sensor 205, data processor 300 automatically inflates balloon members 203, and when the reading process of optical scanner 206 is completed, data processor 300 automatically deflates balloon members 203. However, balloon members 203 may manually be inflated and deflated by the operator.

In the above embodiment, infrared sensor 205 detects when finger F is placed in the readout position of optical scanner 206. However, a pressure sensor (not shown) may be inserted in a base of optical scanner 206 for detecting when finger F contacts optical scanner 206.

In the above embodiment, optical scanner 206 is illustrated by way of example as a data reading means for reading the data of a fingerprint image as biological data. However, the data reading means may comprise an electrostatic scanner, a pressure-sensitive scanner, a heat-sensitive scanner, etc. (not shown).

Figure 8:
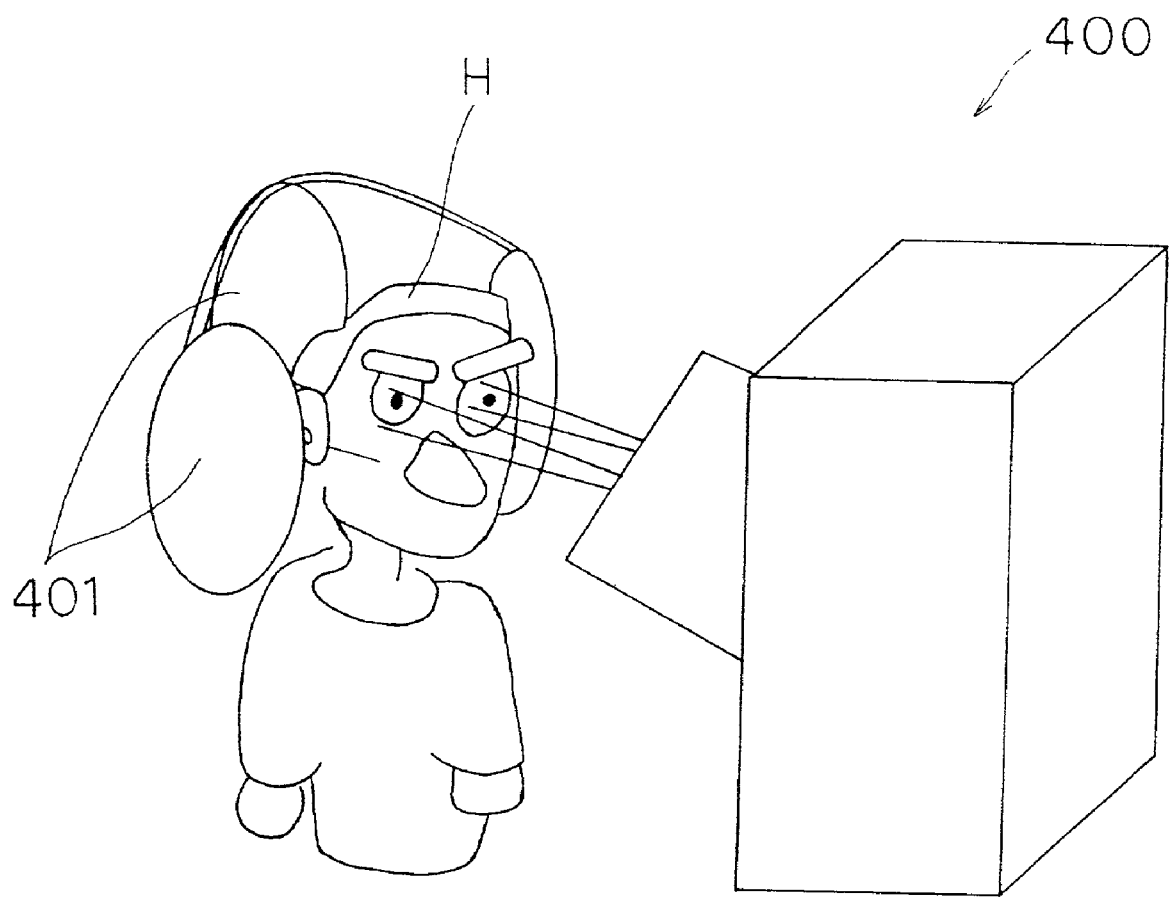
FIG. 8 is a perspective view showing an appearance of a data reader according to a third modification of the present invention.

In the above embodiment, data reader 100 scans finger F, which is a human body region, and reads a fingerprint image there from as biological data while finger F is being constrained by balloon members 203. However, as shown in FIG. 8, the principles of the present invention are also applicable to data reader 400 for reading an eyeprint image as biological data while a head H as a human body region is being constrained by balloon members 401.

While preferred embodiments of the present invention have been described using specific terms, such description is for illustrative purposes only, and it is to be understood that changes and variations may be made without departing from the spirit or scope of the invention.

What is claimed is:

1. A data reader comprising:

a substantially cylindrical cavity in which a finger is freely inserted;

data reading means disposed in said cavity for reading fingerprint data from a said finger placed in a readout position;

region constraining means disposed in said cavity for constraining said finger placed in said readout position; and mode switching means for switching said region constraining means between a mode in which said finger is movable and a mode in which said finger is constrained;

wherein said region constraining means comprises a single annular balloon member which is inflatable and deflatable when a fluid is introduced under pressure into said region constraining means and discharged from said region constraining means, respectively, and said finger is constrained by said balloon member in all directions from the outer circumferential surface of the substantially cylindrical finger to the center of said cavity.

2. A data reader according to claim 1, wherein said mode switching means comprises:

fluid introducing means for introducing said fluid under pressure into said balloon member;

fluid discharging means for discharging said fluid which has been introduced under pressure into said balloon member by said fluid introducing means; and operation control means for controlling operation of said fluid introducing means and said fluid discharging means.

3. A data reader according to claim 2, further comprising:
internal pressure detecting means for detecting the pressure of said fluid introduced under pressure into said balloon member; and
wherein said operation control means comprises means for controlling operation of said fluid introducing means and said fluid discharging means depending on the pressure of the fluid detected by said internal pressure detecting means.

4. A data reader according to claim 1, wherein said fluid comprises a gas.

5. A data reader according to claim 4, wherein said fluid comprises ambient air.

6. A data reader according to claim 1, further comprising
placement detecting means for detecting when said finger is placed in said readout position and inflating said balloon member depending on the detection by said placement detecting mean.

7. A data reader according to claim 6, wherein said placement detecting means comprises means for detecting when said finger contacts said data reading means.

8. A data reader according to claim 1, wherein
said data reading means comprises means for scanning said finger and reading therefrom a fingerprint image as said biological data.

9. A method of reading data with a data reader according to claim 6, comprising the steps of:
controlling said mode switching means to switch said region constraining means to the mode in which said finger is movable;
detecting when said finger is placed in said readout position with said placement detecting means;
controlling said mode switching means to switch said region constraining means to the mode in which said finger is constrained depending on the detection by said placement detecting means;
controlling said data reading means to read said biological data from said finger in said readout position while said finger is being constrained; and
controlling said mode switching means to switch said region constraining means to the mode in which said finger is movable when the reading of said biological data with said data reading means is completed.

10. A data reader according to claim 1, wherein said balloon member has surface irregularities for presenting an increased frictional resistance to said finger.

11. A data reader according to claim 1, wherein said balloon member is disposed at a portion of the finger from which the fingerprint data is not read by the data reading means.

* * * * *